United States Patent [19]
Carls et al.

[11] Patent Number: 5,683,398
[45] Date of Patent: Nov. 4, 1997

[54] DISTAL FEMORAL CUTTING BLOCK ASSEMBLY

[75] Inventors: Thomas A. Carls, Memphis; Steven M. Tammi, Collierville, both of Tenn.

[73] Assignee: Smith & Nephew Inc., Memphis, Tenn.

[21] Appl. No.: 603,982

[22] Filed: Feb. 20, 1996

[51] Int. Cl.$^6$ .................................................. A61B 17/15
[52] U.S. Cl. ................................. 606/89; 606/82
[58] Field of Search ........................ 606/82, 87, 88, 606/89

[56] References Cited

U.S. PATENT DOCUMENTS

| | | |
|---|---|---|
| 4,474,177 | 10/1984 | Whiteside . |
| 4,487,203 | 12/1984 | Androphy . |
| 4,703,751 | 11/1987 | Pohl . |
| 4,721,104 | 1/1988 | Kaufman et al. . |
| 4,722,330 | 2/1988 | Russell et al. . |
| 4,759,350 | 7/1988 | Dunn et al. . |
| 4,773,407 | 9/1988 | Petersen . |
| 4,892,093 | 1/1990 | Zarnowski et al. . |
| 4,935,023 | 6/1990 | Whiteside et al. . |
| 5,282,803 | 2/1994 | Lackey .................................. 606/88 |

*Primary Examiner*—Michael Buiz
*Assistant Examiner*—Daphna Shai
*Attorney, Agent, or Firm*—Pravel, Hewitt, Kimball & Krieger

[57] ABSTRACT

A composite cutting block for preparing a patient's distal femur to receive a knee prosthesis includes a first block body having a triangular cross section that engages the patient's distal femur using bone tissue connectors such as bone spikes. A pair of inclined surfaces form acute angles with a flat surface, the inclined surfaces defining anterior and posterior chamfer cutting guide surfaces. A second block body has an undersurface with an elongated inverted "T" shaped slot. The first block body fits the slot so that the flat distal surfaces of the first block body and the flat distal surface of the second block body are in planes that are closely positioned upon assembly. A connector in the form of a threaded shaft holds the first block body in the slot of the second block body to define an assembled position. The second block body has opposed parallel cutting guide surfaces that are perpendicular to the undersurface of the second block body for enabling the surgeon to make anterior and posterior cuts on the a patient's distal femur. During use, the second block forms a guard over the first block body when a surgeon is making the anterior and posterior cuts. The surgeon then removes the second block body to expose the first block body so that the anterior and posterior chamfer cuts can be made.

14 Claims, 5 Drawing Sheets

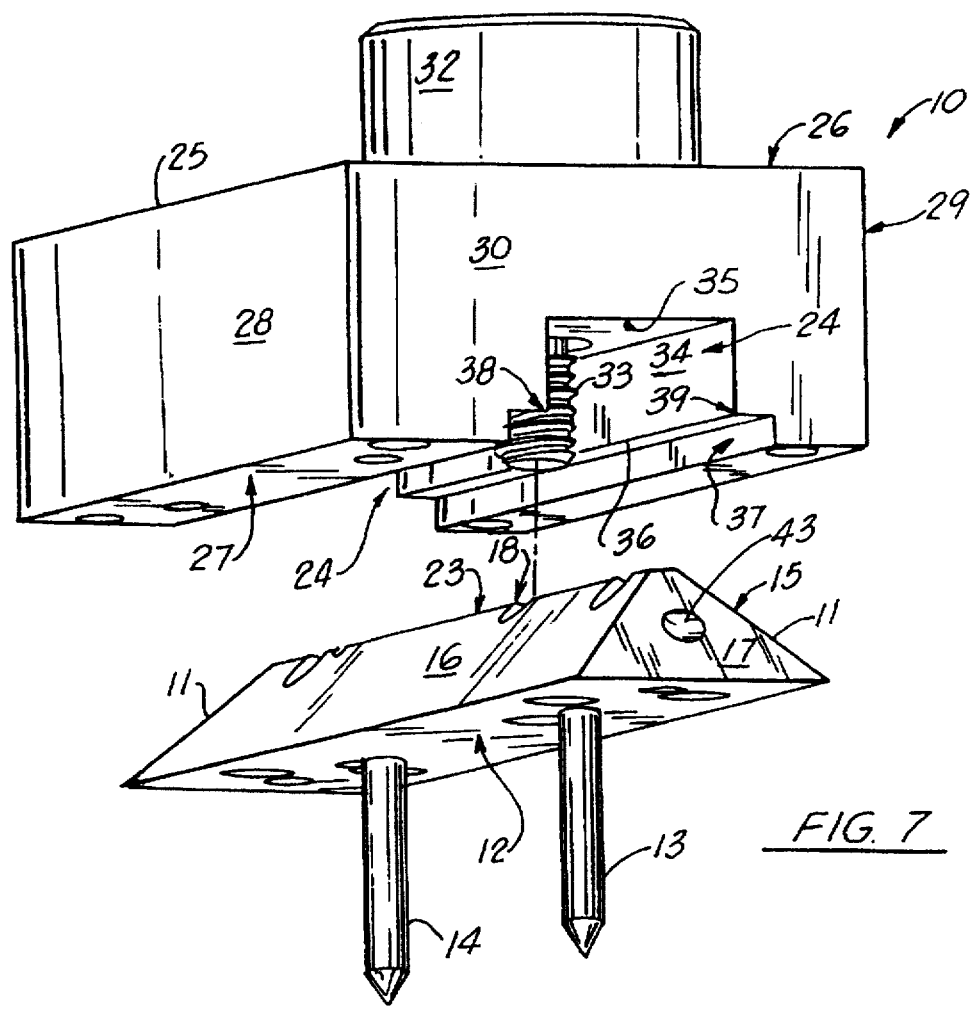
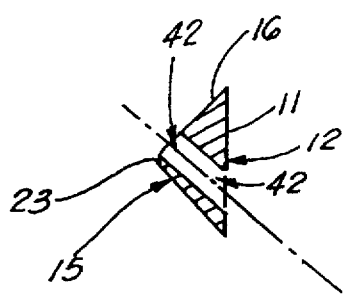
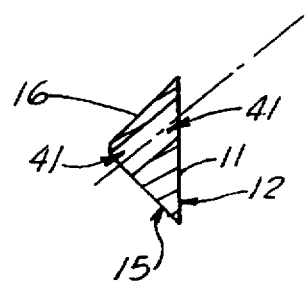
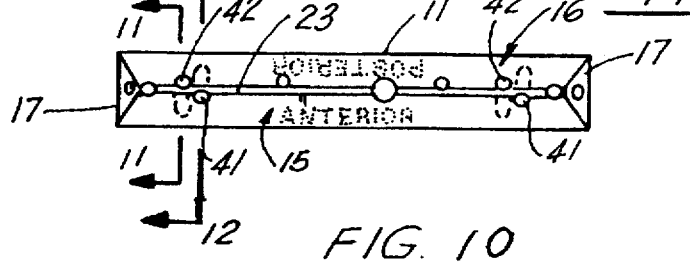

5,683,398

DISTAL FEMORAL CUTTING BLOCK ASSEMBLY

BACKGROUND OF THE INVENTION

1. Field of the Invention

The present invention relates to an orthopedic surgical instrument, namely an improved orthopedic distal femoral cutting block assembly. More particularly, the present invention relates to an improved distal femoral cutting block assembly that includes a first cutting block that nests in a slot provided on a second cutting block so that the second cutting block hides the first cutting block until certain cuts are made using the second block on the distal femur by a surgeon. Even more particularly, the present invention relates to a composite cutting block having an improved three point attachment that holds first and second cutting blocks together, wherein two cutting blocks are separable so that cuts can be made on the distal femur using selected surfaces of the assembly of the two blocks or using surfaces on the first block after the two blocks are separated.

2. General Background

In knee joint replacement surgery, a distal femoral component is placed upon the patient's distal femur. A cooperating tibial component is placed on the patient's proximal tibia. A common type of femoral prosthesis is a generally "J" shaped prosthesis that provides a curved articulating surface that can include one or two condylars portions.

Many of these commercially available femoral components have five flat surfaces on the rear or proximal side of the femoral implant. In order to mount this type of implant on the patient's distal femur, the surgeon must make five cuts on the distal femur that correspond to the five flat surfaces on the prosthesis. These five cuts are known in the art as the distal femoral cut, the anterior and posterior cuts, and the anterior chamfer and posterior chamfer cuts.

Cutting blocks are presently commercially available that allow the surgeon to make these five cuts. There are also cutting block systems that comprise two separate cutting blocks including the first block for making the anterior and posterior cuts and a different block that makes the diagonally extending anterior chamfer and posterior chamfer cuts.

Many cutting blocks for preparing a patient's bone tissue to receive a knee prosthesis have been patented. The Whiteside U.S. Pat. No. 4,474,177 provides a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. The intramedullary alignment guide has a rod portion extending into the femoral intramedullary canal whose central long axis corresponds with the central long axis of the femur. The guide handle is attached to that rod portion at a preselected angle such that the shaping instruments fixed thereto assume the proper alignment with respect to the central long axis of the femur such that the distal femoral surface is shaped relative to that axis in a simple and accurate manner.

A triplanar knee resection system for preparing a knee joint for a prosthesis is disclosed in U.S. Pat. No. 4,487,203. The apparatus includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by ann orthopedic surgeon in properly preparing a knee joint for implantation of a prosthesis.

A method and apparatus for resecting a distal femoral surface is disclosed in U.S. Pat. No. 4,703,751 in which an intramedullary rod is inserted through the distal surface of the femur and along the femoral shaft access, leaving a protruding end. A jig is attached to the protruding end, the jig having a shaft for receiving the rod end and a support plate attached to an end of the shaft and extending parallel to the rod, attaching a reference bar to the shaft. The bar provides a pair of opposing flanges and a central opening which receives the shaft therethrough. Adjusting the bar on the shaft is such that the flanges contact condylar apices of the femur and fixing the jig relative to the femur. A cutting plate has blade guides thereon, pivoting the cutting plate relative to the jig such that the blade guides made a predetermined angle with the rod, securing the cutting plate to the jig, and inserting a saw blade through the blade guides to make a resection of the distal femoral surface.

The Kaufman et al. U.S. Pat. No. 4,721,104 relates to a surgical apparatus for providing an accurately recess in a distal femoral surface for the intercondylar stabilizing housing of a posterior-stabilized knee implant prosthesis.

The Russell et al. U.S. Pat. No. 4,722,330 relates to distal femoral surface shaping guide for mounting on a intramedullary alignment guide which references the central long axis of the femur in shaping the distal femoral surface and a method for shaping the distal femur using the shaping guide.

The Dunn et al. U.S. Pat. No. 4,759,350 provides a system of instruments for shaping the distal femur and proximal tibia surfaces to receive components of a knee prosthesis for knee replacement surgery. The system references the femur intramedullary channel with a femoral alignment guide to prepare the distal femur that, in turn, is a reference for several cutting guides for sequential attachment to the femoral alignment guide and prepared bone surfaces whereby the prepared distal femur is prepared to a flat surface that is perpendicular to the patient's mechanical axis with bone surfaces adjacent thereto sectioned to surfaces that are at right angles to that distal femur surface with chamfers therebetween to receive the femur component of a knee prosthesis.

U.S. Pat. No. 4,773,407 issued to Petersen discloses a method and instruments for resection of the distal femur. The instruments include a distal femoral resector and a femoral alignment guide/rod. The distal femoral resector is designed to be attached to the distal femur on a plane filed on the anterior femoral cortex. The distal femoral resector includes a feeler gauge laterally adjustable to adapt to the intercondylar notch of the particular patient and further includes a rotating rod having openings therethrough for fastening pins, which rotating rod is designed to facilitate the placement of the resector on the anterior femoral cortex in a flush manner. The femoral alignment guide/rod includes a plate insertable within a slot in the resector designed for the insertion of the cutting tool and further includes a pivotable rod which may be utilized to align the resector with the mechanical axis of the leg. The rod may then be pivoted to a position facilitating the insertion of a fastening pin through the resector. The method of operation using these instruments is also disclosed.

U.S. Pat. No. 4,892,093 issued to Zarnowski et al. discloses a cutting guide for guiding a saw blade during the preparation of a femur for the implant of the femoral component of a knee prothesis includes guide surfaces for enabling the cutting of all four of the anterior femoral cut, the posterior femoral cut, the anterior chamfer and the posterior chamfer, fully and completely, with certitude and accuracy, while the cutting guide remains located and secured to the femur in a single position on a transverse surface located along the distal femur.

The Whiteside et al. U.S. Pat. No. 4,935,023 relates to a distal femoral surface shaping guide for mounting on an intramedullary alignment which references the central long axis of the femur in shaping the distal femoral surface and a method for shaping the distal femur using that shaping guide with particular applicability for shaping one condyle for attachment of a unicondylar prosthesis.

SUMMARY OF THE INVENTION

The present invention provides an improved cutting block apparatus for preparing a patient's distal femur to receive a knee prosthesis.

The apparatus of the present invention includes a first block body having a triangular cross section that is defined by a distal flat surface adapted to engage the patient's distal femur, and a pair of inclined surfaces that each form an acute angle with the distal flat surface. The two inclined surfaces define anterior and posterior chamfer cutting guide surfaces.

A surgeon can track the inclined surfaces one at a time for making the anterior chamfer and the posterior chamfer cuts on the patient's distal femur. During a cutting of the femur with the first block, the flat distal surface of the first cutting block rests against the flat surface of the surgically prepared distal femur that has already received a transverse distal cut.

A second block body provides an undersurface with an elongated slot that extends between the medial and lateral sides of the block. The second block body can be of a rectangular prism shape, providing flat preferably parallel upper and lower or proximal and distal planar surfaces, flat, preferably parallel medial and lateral surfaces, and flat preferably parallel anterior and posterior surfaces.

The slot is an elongated slot that extends between the medial and lateral surfaces and communicates with the flat distal or lower surface. The slot has a "T" shaped transverse cross sectional configuration providing a thinner portion and a wider portion with a knife edge in between. The opposed knife edges of the elongated slot define bearing points that bear against the inclined surfaces of the first block body when the first and second block bodies are assembled.

A connector is provided for holding the first block body in the slot of the second block body to define an assembled position of the two blocks.

An anchor on the assembly of the first block body and the second block body is provided for anchoring the assembly of the first and second block bodies to the patient's distal femur. In the preferred embodiment, the anchor is in the form of a pair of spaced apart bone spikes that extend perpendicularly to the flat distal surfaces of the first block body.

The anterior and posterior flat surfaces of the second block body define opposed cutting guide surfaces that are each generally perpendicular to the undersurface of the second block body. The surgeon uses these two opposed, anterior and posterior surfaces for making anterior and posterior cuts on a patient's distal femur after the assembly of the first and second block bodies have been attached to the distal femur.

During this cutting of the anterior and posterior cuts, the second block is attached to and forms a guard over the first block. This requires the surgeon to first make the anterior and posterior cuts and only after the assembly of the first and second blocks is affixed to the patient's distal femur in a desired position.

Because the first and second blocks are attached, orientation of the first block body is automatic when the two block bodies are attached to the patient's distal femur. This is because of a removable but rigid three point connection between the first and second block bodies. Since the overall assembly of the first and second block bodies properly orients the two relative to one another, all cuts will be properly oriented. When the surgeon finishes making anterior and posterior cuts, the second block body can be removed exposing the first block body and its anterior and posterior angled surfaces.

With the second block body removed, the surgeon has full view of the anterior and posterior chamfer cutting guide surfaces of the first block body and is assured that those surfaces are properly oriented relative to the anterior and posterior cuts that were made using the second block body.

In the preferred embodiment, a knob with a threaded shaft extends through an opening of the second block body and engages an internally threaded opening of the first block body. The knife edges of the elongated slot on the second block body in combination with the threaded engagement of the shaft and internally threaded opening ensures a three point geometric contacting surface that always orients the first and second block bodies properly relative to one another.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 7 is another perspective view of the preferred embodiment of the apparatus of the present invention;

FIG. 10 is a partial proximal view of the preferred embodiment of the apparatus of the present invention illustrating the first cutting block portion thereof;

FIG. 11 is a sectional view taken along lines 11—11 of FIG. 10; and

FIG. 12 is a sectional view taken along lines 12—12 of FIG. 10.

DETAILED DESCRIPTION OF THE PREFERRED EMBODIMENT

FIGS. 1–3 and 7–9 show generally the preferred embodiment of the apparatus of the present invention designated generally by the numeral 10. Knee cutting instrument 10 includes a first cutting block 11 having a flat distal surface 12 that is to be positioned by the surgeon upon the flat surgically prepared distal femur after the surgeon has formed a distal femoral cut. The knee cutting instrument 10 of the present invention can be used to form anterior and posterior cuts and the anterior and posterior chamfer cuts.

Figure 1:
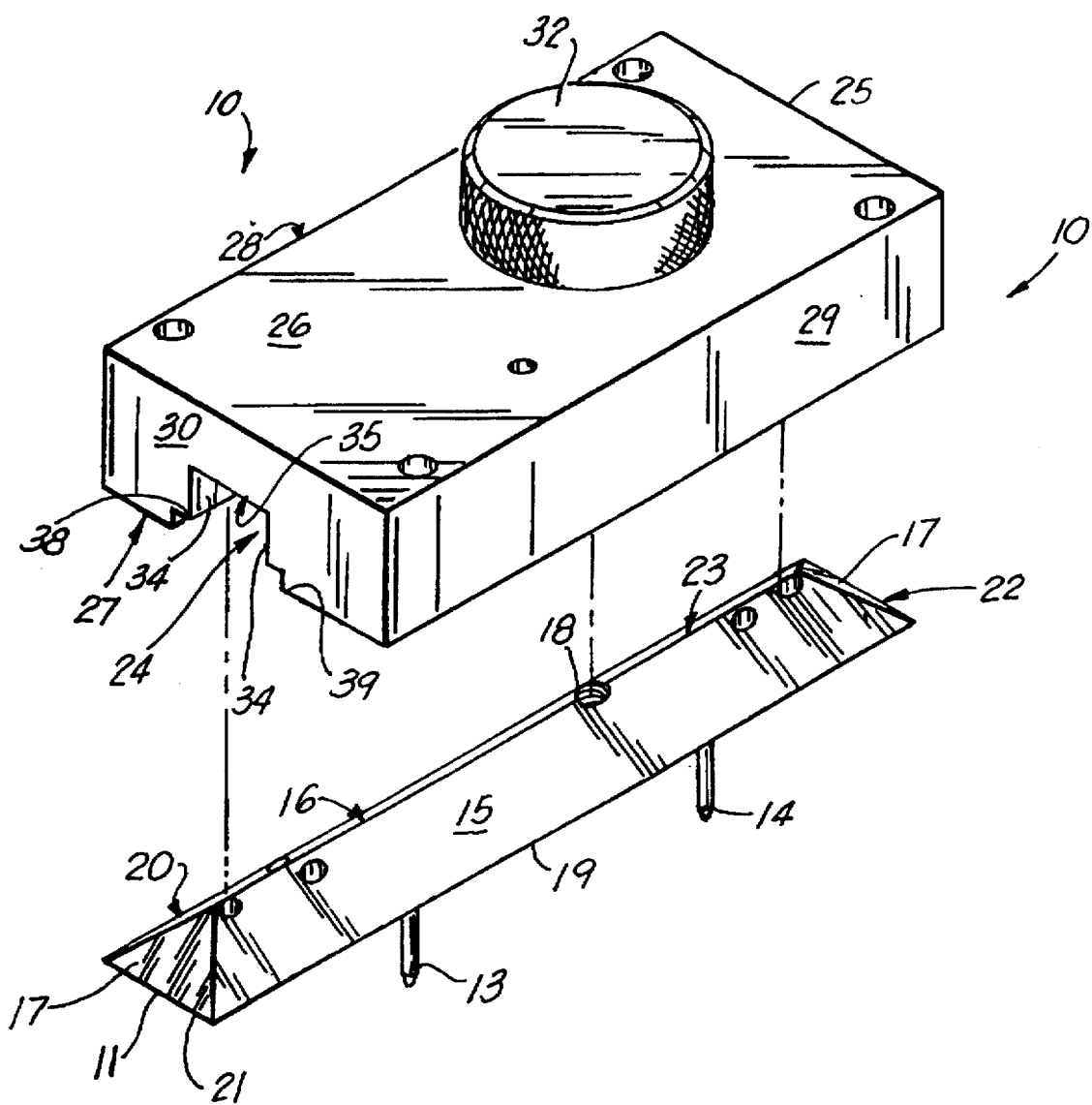
FIG. 1 is a perspective exploded view of the preferred embodiment of the apparatus of the present invention.
Figure 2:
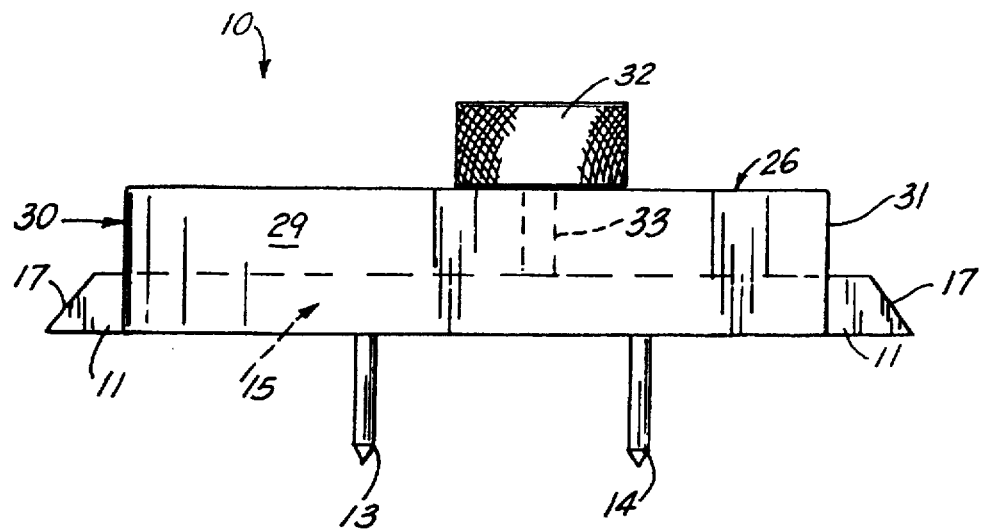
FIG. 2 is an elevational view thereof.
Figure 4:
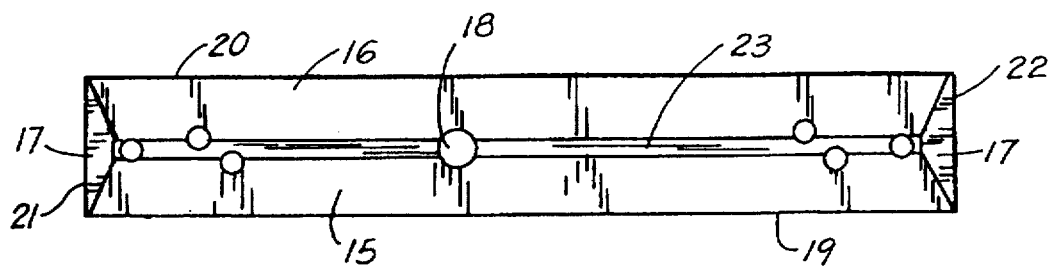
FIG. 4 is a top view of the first cutting block portion of the preferred embodiment of the apparatus of the present invention.

The assembly of knee cutting instrument 10 includes bone spikes 13, 14 for attaching the knee cutting instrument 10 to the patient's distal femur. In the preferred embodiment, the two bone spikes 13, 14 extend perpendicularly from flat distal surface of the first cutting block 11. The first cutting block 11 provides a pair of diagonally extending surfaces 15, 16 that each form an acute angle with flat distal surface 12. The end portions of first cutting block 11 can be angled as shown with end surfaces 17. The periphery of first cutting block 11 includes edge portions 19, 20, 21, 22 as shown in FIGS. 1 and 4.

Diagonally extending surfaces 15, 16 intersect along apex 23. Slot 24 holds the first cutting block 11 when it attaches to second cutting block 25 as shown in FIGS. 1, 3 and 6–9. Slot 24 is sized and shaped to hold the first cutting block 11 so that the distal surface 12 of first cutting block 11 is in the same plane 40 with the distal surface 27 of second cutting block 25. The slot 24 can be sized and shaped to place the first cutting block 11 in a position so that the distal surface 12 of the first cutting block 11 is nested within the slot 24 and slightly below the plane 40. The plane 40 is defined by distal surface 27 of second cutting block 25. It is desired that the surface 12 rest upon on the prepared distal surface of the bone.

Second cutting block 25 has a flat proximal surface 26, a flat distal surface 27, and flat anterior and posterior surfaces 28, 29. The sides of second cutting block 25 define flat parallel medial and lateral surfaces 30, 31.

Figure 5:
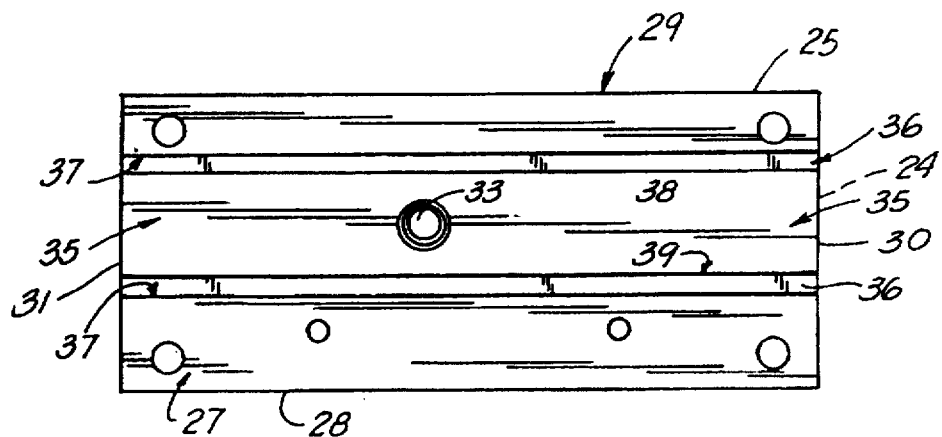
FIG. 5 is a bottom view of the second cutting block portion of the preferred embodiment of the apparatus of the present invention.
Figure 6:
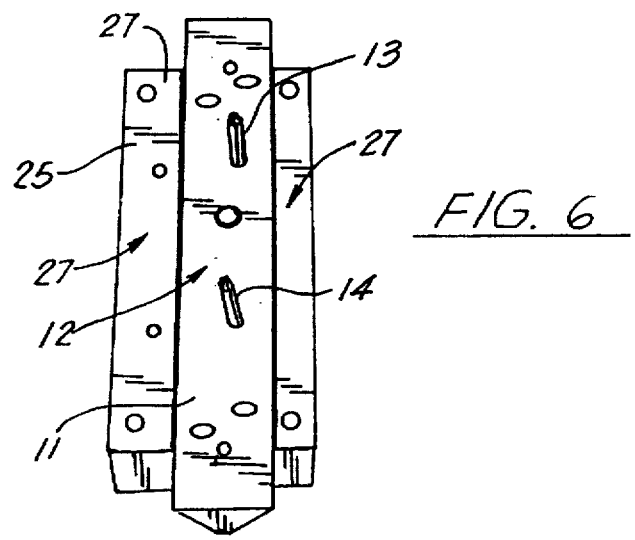
FIG. 6 is perspective view of the preferred embodiment of the apparatus of the present invention.
Figure 8:
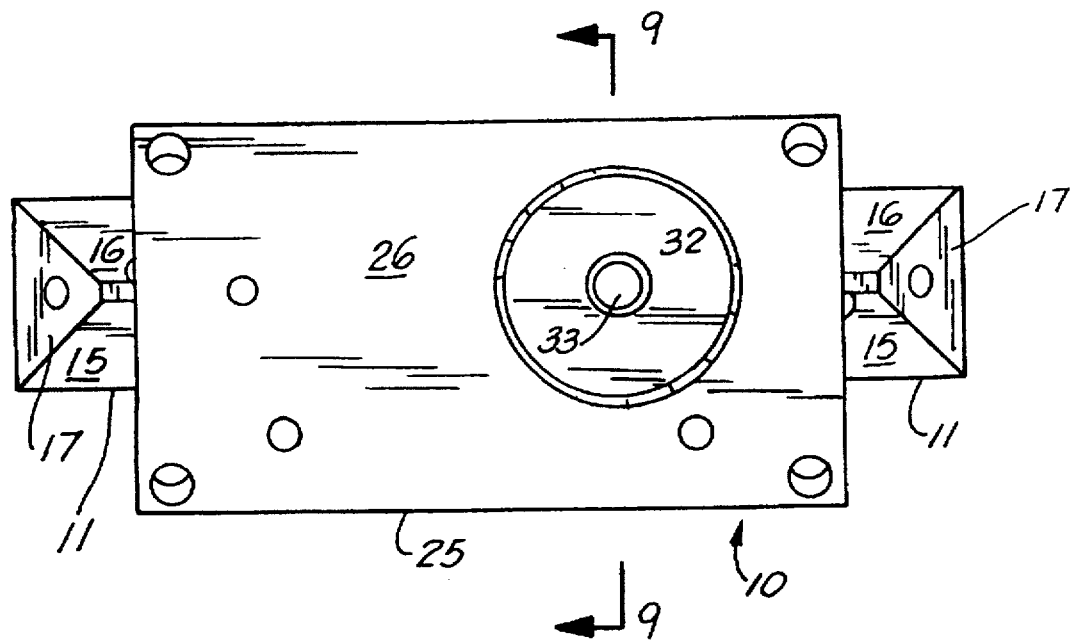
FIG. 8 is a proximal view of the preferred embodiment of the apparatus of the present invention.
Figure 9:
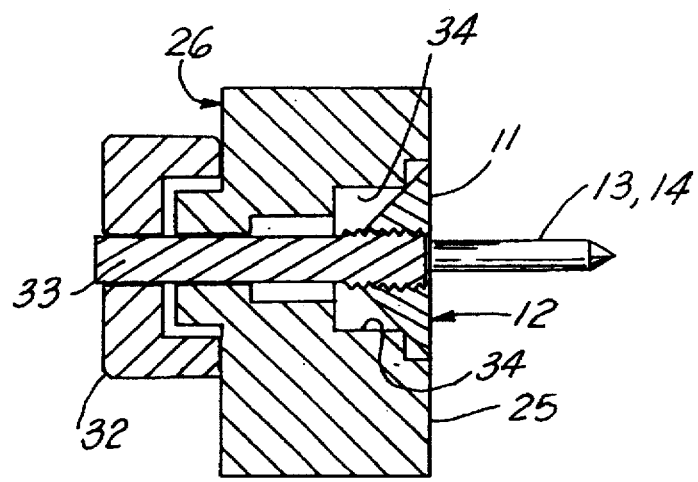
FIG. 9 is a sectional view taken along lines 9—9 of FIG. 8.

The first 11 and second 25 cutting blocks can be assembled using knob 32 and its attached threaded shaft 33. The user simply rotates the knob 32 so that the shaft 33 rotates therewith. An internally threaded opening 18 on first cutting block 11 receives and engages shaft 33. The threaded opening 18 is a cylindrically shaped opening having a central axis that is perpendicular to the flat distal surface 12 of first cutting 11. Slot 24 is defined by a plurality of flat surfaces 34, 35, 36, 37 as shown in FIGS. 1, 3 and 5.

Figure 3:
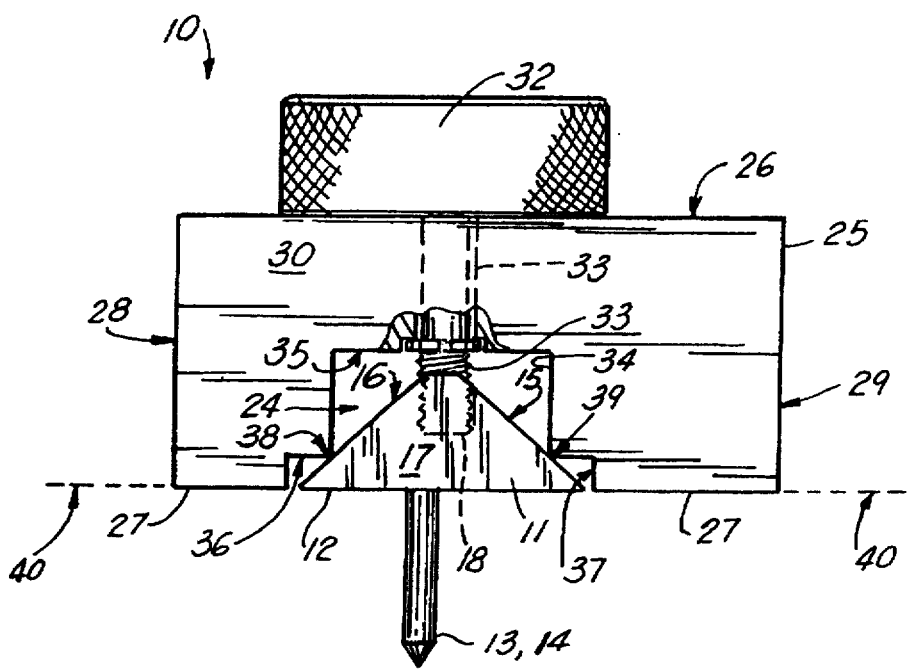
FIG. 3 is a side view thereof.

In FIG. 3, the slot 24 is generally "T" shaped having a smaller thickness slot portion defined by surfaces 34 and 35 and a larger thickness slot portion defined by surfaces 36 and 37. The intersection of surfaces 34 and 36 is defined by the opposed sharp edge portions 38, 39. Upon assembly of first and second cutting blocks 11, 25 the diagonally extending surfaces 15, 16 engage the sharp edges 38, 39 as shown in FIG. 3.

Internally threaded opening 18 is centered in apex 23 as shown in FIG. 4. Thus, a three point contact is defined between the block 11 and block 25 as shown in FIG. 3. This three point attachment is defined by the threaded engagement of shaft 33 and opening 18 as well as the engagement of the sharp edges 38, 39 against the diagonally extending surfaces 15, 16. Upon assembly of first and second blocks 11 and 25, FIG. 3 shows that a small gap is positioned between the edges 19 and 20 of first cutting block 11 and the second cutting block 25.

In FIGS. 10–12, block 11 can have a pair of diagonally extending bores 41 that extend between surfaces 15 and 12. The bores 41 can be angled relative to surface 16 (see FIG. 12). The bores 42 can be angled relative to surface 15 (see FIG. 11). These bores 41, 42 enable the surgeon to attach a saw capture (not shown) to the cutting block 11 at either surfaces 15 or 16. These are angled openings 43 (see FIGS. 1 and 7) at end surfaces 17 that can accept a bone spike.

The following table lists the parts numbers and parts descriptions as used herein and in the drawings attached hereto.

| PARTS LIST | |
|---|---|
| Part Number | Description |
| 10 | knee cutting instrument |
| 11 | first cutting block |
| 12 | flat distal surface |
| 13 | bone spike |
| 14 | bone spike |
| 15 | diagonally extending surface |
| 16 | diagonally extending surface |
| 17 | angled end surfaces |
| 18 | threaded opening |
| 19 | edge |
| 20 | edge |
| 21 | edge |
| 22 | edge |
| 23 | apex |
| 24 | slot |
| 25 | second cutting block |
| 26 | flat proximal surface |
| 27 | distal surface |
| 28 | anterior surface |
| 29 | posterior surface |
| 30 | medial surface |
| 31 | lateral surface |
| 32 | knob |
| 33 | threaded shaft |
| 34 | flat surface |
| 35 | flat surface |
| 36 | flat surface |
| 37 | flat surface |
| 38 | edge |
| 39 | edge |
| 40 | plane |
| 41 | bore |
| 42 | bore |
| 43 | opening |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A composite femoral cutting block for preparing a patient's distal femur to receive a knee prosthesis comprising:
    a) a first block body having a triangular cross section defined by a flat surface that is adapted to engage the patient's distal femur and a pair of included surfaces that each form an acute angle with the flat surface, wherein the inclined surfaces define anterior and posterior chamfer cutting guide surfaces for making anterior chamfer and posterior chamfer cuts on the patient's distal femur;

b) a second block body having an undersurface with an elongated slot, the first block fitting the slot so that the flat surface of the first block body is generally parallel to the distal surface of the second block body;

c) the first and second block bodies being separate members that can be removed one at a time from the patient's distal femur;

d) a connector for holding the first block body in the slot of the second block body to define an assembled position;

e) the assembly of the first block body and second block body having an attachment for anchoring the assembly of the first block body and the second block body to the patient's distal femur;

f) the second block body having opposed, cutting guide surfaces that are each angled with respect to the undersurface of the second block; and g) the second block forming a guard over the first block upon assembly.

2. The composite femoral cutting block of claim 1 wherein the attachment comprises one or more openings on the assembly through which bone pins or bone screws can be inserted into underlying bone tissue.

3. The composite femoral cutting block of claim 1 wherein the attachment comprises one or more bone spikes mounted on the assembly.

4. The composite femoral cutting block of claim 1 wherein the first block body and second block body have undersurface portions that are in planes the are closely positioned upon assembly.

5. The composite femoral cutting block of claim 1 wherein the second cutting block has an undersurface within an elongated slot that is "T" shaped in transverse cross section.

6. The composite femoral cutting block of claim 1 wherein the second block has parallel anterior and posterior surfaces.

7. The composite femoral cutting block of claim 1 wherein the second block body has parallel proximal and distal surfaces.

8. The composite femoral cutting block of claim 1 wherein the connector comprises a threaded member on one of the block bodies and an internally threaded opening on the other of the block bodies.

9. The composite femoral cutting block body of claim 8 wherein the first and second block bodies are connected at three positions including first and second positions at the two inclined surfaces of the first block body and a third position at an apex portion of the first block body.

10. The composite femoral cutting block of claim 1 wherein the anchor comprises at least one bone spike.

11. The composite femoral cutting block of claim 1 wherein the second block has an elongated slot that includes two elongated portions that engage that inclined surfaces of the first block body upon assembly.

12. The composite femoral cutting block of claim 1 wherein the connector includes a threaded connector that extends between the first and second block bodies at the apex portion of the first block body.

13. A composite femoral cutting block for preparing a patient's distal femur to receive a knee prosthesis comprising:

a) a first block body having a triangular cross section defined by a flat surface that is adapted to engage the patient's distal femur and a pair of included surfaces that each form an acute angle with the flat surface, wherein the inclined surfaces define anterior and posterior chamfer cutting guide surfaces for making anterior chamfer and posterior chamfer cuts on the patient's distal femur and wherein the surgeon can view substantially the entire surface of each inclined surface;

b) a second block body having an undersurface with an elongated slot, the first block fitting the slot so that the flat surface of the first block body is generally parallel to the distal surface of the second block body;

c) the first and second block bodies being separate members that can be removed one at a time from the patient's distal femur;

d) a connector for holding the first block body in the slot of the second block body to define an assembled position;

e) the assembly of the first block body and second block body having an attachment for anchoring the assembly of the first block body and the second block body to the patient's distal femur;

f) the second block body having opposed, cutting guide surfaces that are each angled with respect to the undersurface of the second block; and g) the second block forming a guard over the first block upon assembly.

14. A composite femoral cutting block for preparing a patient's distal femur to receive a knee prosthesis comprising:

a) a first block body having a triangular cross section defined by a flat surface that is adapted to engage the patient's distal femur and a pair of included surfaces that each form an acute angle with the flat surface, wherein the inclined surfaces define anterior and posterior chamfer cutting guide surfaces for making anterior chamfer and posterior chamfer cuts on the patient's distal femur and wherein the surgeon can view substantially the entire surface of each inclined surface;

b) a second block body having an undersurface with an elongated slot, the first block fitting the slot so that the flat surface of the first block body is generally parallel to the distal surface of the second block body;

c) the first and second block bodies being separate members that can be removed one at a time from the patient's distal femur;

d) a connector for holding the first block body in the slot of the second block body to define an assembled position and for disassembling one block from the other, even when the blocks are positioned on the patient's distal femur;

e) the assembly of the first block body and second block body having an attachment for anchoring the assembly of the first block body and the second block body to the patient's distal femur;

f) the second block body having opposed, cutting guide surfaces that are each angled with respect to the undersurface of the second block; and g) the second block forming a guard over the first block upon assembly.

* * * * *